(12) United States Patent
Chen

(10) Patent No.: US 8,756,032 B2
(45) Date of Patent: Jun. 17, 2014

(54) METHOD AND APPARATUS FOR FALL DETECTION

(75) Inventor: Ningjiang Chen, Shanghai (CN)

(73) Assignee: Koninklijke Philips N.V., Eindhoven (NL)

( * ) Notice: Subject to any disclaimer, the term of this patent is extended or adjusted under 35 U.S.C. 154(b) by 320 days.

(21) Appl. No.: 13/130,780

(22) PCT Filed: Nov. 19, 2009

(86) PCT No.: PCT/IB2009/055162
§ 371 (c)(1),
(2), (4) Date: May 24, 2011

(87) PCT Pub. No.: WO2010/061321
PCT Pub. Date: Jun. 3, 2010

(65) Prior Publication Data
US 2011/0231145 A1    Sep. 22, 2011

(30) Foreign Application Priority Data

Nov. 28, 2008  (CN) .......................... 2008 1 0178339

(51) Int. Cl.
*G01P 15/00*   (2006.01)
(52) U.S. Cl.
USPC ......... 702/141; 73/12.01; 73/12.04; 73/12.06
(58) Field of Classification Search
USPC ................... 702/141; 73/12.01, 12.04, 12.06; 600/581, 595
See application file for complete search history.

(56) References Cited

U.S. PATENT DOCUMENTS

| 6,201,476 | B1 * | 3/2001 | Depeursinge et al. ..... 340/573.1 |
| 2001/0004234 | A1 | 6/2001 | Petelenz et al. |
| 2005/0067816 | A1 | 3/2005 | Buckman |
| 2005/0093709 | A1 | 5/2005 | Franco, Jr. et al. |
| 2006/0116848 | A1 * | 6/2006 | Clifford et al. ............... 702/141 |
| 2006/0214806 | A1 | 9/2006 | Clifford et al. |
| 2007/0225947 | A1 * | 9/2007 | Suzuki ......................... 702/189 |
| 2011/0144542 | A1 * | 6/2011 | Jin et al. ....................... 600/595 |

FOREIGN PATENT DOCUMENTS

| EP | 1779772 A1 | 5/2007 |
| EP | 1870037 A1 | 12/2007 |
| WO | 2008091227 A1 | 7/2008 |
| WO | WO 2008129451 A1 * | 10/2008 ............... A61B 5/11 |

OTHER PUBLICATIONS

Weir, Thomas' Calculus Early Transcendentals, 2006, Pearson Education, pp. 446-447.*
Flash et al: "The Coordination of Arm Movements: An Experimentally Confirmed Mathematical Model"; The Journal of Neuroscience, vol. 5, No. 7, Jul. 1985, pp. 1688-1703.

(Continued)

*Primary Examiner* — John Breene
*Assistant Examiner* — Stephanie Bloss

(57) ABSTRACT

A method for detecting the fall of an object includes: acquiring a plurality of time-varying accelerations associated with a movement of said object; computing a plurality of respective velocities and displacements in the direction of gravity, based on the plurality of time-varying accelerations; determining lead time and return time of the movement, based on the plurality of accelerations, velocities and displacements, wherein the lead time equals a time interval from an original point of the movement to an extreme point of the movement, and the return time equals a time interval from the extreme point of the movement to a final point of the movement; and determining whether the fall of said object occurs, based on whether a peak value of the velocities is larger than a predefined threshold value and whether the lead time is longer than the return time.

20 Claims, 8 Drawing Sheets

(56) References Cited

OTHER PUBLICATIONS

Degen et al: "Speedy: A Fall Detector in a Wrist Watch"; Proceedings of the Seventh IEEE International Symposium on Wearable Computers (ISWC'03), 2003, pp. 184-187.

Bourke et al: "Distinguishing Falls From Normal ADL Using Vertical Velocity Profiles"; Conference Proceedings of teh International Conference of IEEE Engineering in Medicine and Biology Society, 2007, pp. 3176-3179.

* cited by examiner

METHOD AND APPARATUS FOR FALL DETECTION

FIELD OF THE INVENTION

The invention relates to fall detection, particularly to a method and apparatus for fall detection.

BACKGROUND OF THE INVENTION

A fall is defined as a sudden, uncontrolled and unintentional downward displacement of the body to the ground. Falls affect millions of people every year and result in significant injuries, particularly in the elderly. In fact, falls have been estimated to be among the top three causes of death in elderly people.

There are currently some fall detection apparatus available that detect these falls and allow the user to obtain assistance manually or automatically if a fall occurs. One example of a fall detection apparatus detects falls in accordance with the velocity profile of a user in the vertical direction, since a vertical body movement in the direction of gravity occurs during the fall. If the maximum velocity in the direction of gravity is larger than a threshold, it is determined in such an apparatus that a fall occurs.

However, this threshold is only suitable when the accelerometer is worn on the torso. If the sensor is worn on the wrist, other activities, such as waving or shaking hands, may also involve wrist movement at a velocity as high as falls. Therefore, the maximum velocity cannot be used as a reliable feature to distinguish falls from other activities.

Thomas Degen et al. (see "Speedy: a Fall Detector in a Wrist Watch", Proceedings of the Seventh IEEE International Symposium on Wearable Computers (2003), Page(s): 184-187, the contents thereof are herein incorporated by reference) proposed a wrist-worn fall detector for elderly people. It is compact and easy to use.

However, this detector still uses the simple criteria of determining whether a fall occurs if the maximum velocity is larger than a predetermined threshold (in the above document, the velocity threshold for fall detection is $1.3 \text{ ms}^{-1}$). Since the hands play a very important role in our daily lives, this detection method usually results in a false alarm in activities in which the velocities of hands are larger than the threshold, for example, in handshaking.

OBJECT AND SUMMARY OF THE INVENTION

It is an object of the invention to provide an easy-to-wear and comfortable apparatus for fall detection with less false alarm than fall detectors of the prior art.

To this end, the present invention provides a method and apparatus for fall detection to solve the above-mentioned problems.

According to one aspect of the present invention, a method is provided for detecting the fall of an object, said method comprising the steps of:

acquiring a plurality of time-varying accelerations associated with a movement of said object;

computing a plurality of respective velocities and displacements in the direction of gravity, based on the plurality of time-varying accelerations;

determining lead time and return time of the movement, based on the plurality of accelerations, velocities and displacements, wherein the lead time equals a time interval from an original point of the movement to an extreme point of the movement, and the return time equals a time interval from the extreme point of the movement to a final point of the movement; and determining whether the fall of said object occurs, based on whether a peak value of the velocities is larger than a predefined threshold value and whether the lead time is longer than the return time.

Since determination of a fall does not only include a criterion that the maximum velocity in the direction of gravity must exceed a threshold but also includes a criterion that the lead time must be longer than the return time, wherein the lead time and the return time representing the difference between the fall and other daily activities can be used as a feature to distinguish falls from other activities, the rate of false alarms is reduced, resulting in an improved reliability of fall detection.

In another embodiment, the method further comprises the steps of:

computing smoothness of time-varying velocities based on the plurality of velocities;

determining whether the smoothness is larger than a predefined smoothness threshold; and determining that the fall of said object occurs when the smoothness is larger than the predefined smoothness threshold and the lead time is longer than the return time.

Since in addition to the lead time and the return time representing the difference between the fall and other daily activities, the smoothness of the velocity profile can also be used as a feature to distinguish falls from other activities, the reliability of fall detection is further improved.

According to another aspect of the present invention, an apparatus is provided for detecting the fall of an object, said apparatus comprising:

an acquiring unit configured to acquire a plurality of time-varying accelerations associated with a movement of said object;

a first computing unit configured to compute a plurality of respective velocities and displacements in the direction of gravity, based on the plurality of time-varying accelerations;

a first determining unit configured to determine lead time and return time of the movement, based on the plurality of accelerations, velocities and displacements, wherein the lead time equals a time interval from an original point of the movement to an extreme point of the movement, and the return time equals a time interval from the extreme point of the movement to a final point of the movement; and a second determining unit configured to determine whether a fall of said object occurs, based on whether a peak value of the velocities is larger than a predefined threshold value and whether the lead time is longer than the return time.

Other objects and results of the present invention will become more apparent and easily understood from the description with reference to the accompanying drawings.

DESCRIPTION OF THE DRAWINGS

The present invention will be described and explained hereinafter in more detail with reference to embodiments and the drawings, in which.

The same reference signs in the Figures indicate similar or corresponding features and/or functionalities.

DESCRIPTION OF EMBODIMENTS

Figure 1:
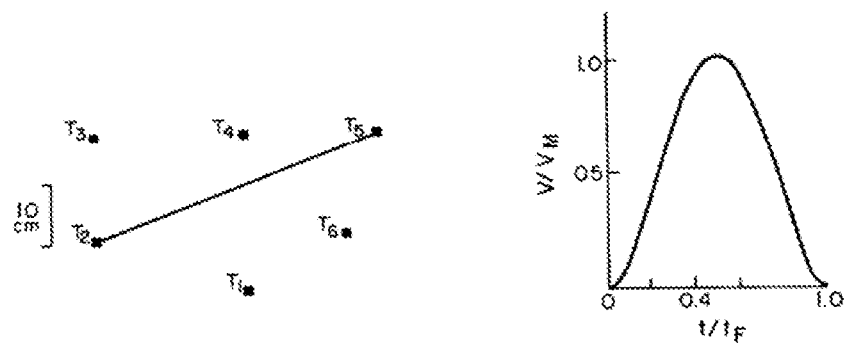
FIG. 1 shows a velocity profile of an arm movement in a straight line.
Figure 2:
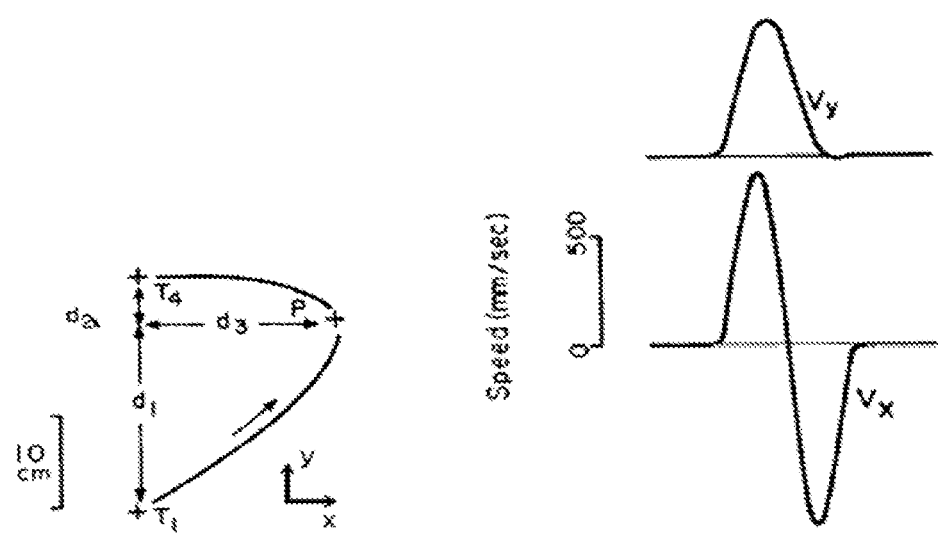
FIG. 2 shows a velocity profile of an arm movement in a curved line.

FIG. 1 shows a velocity profile of an arm movement in a straight line and FIG. 2 shows a velocity profile of an arm movement in a curved line.

As shown in FIG. 1, when people move their arms in a straight line in daily activities, the velocity profile of the arm is a bell shape. If the arm is moved in a curved line, the velocity profile consists of several bell shapes as shown in FIG. 2, each of which corresponds to one segment divided by inflexions, such as the P point in the Figure. It can also be found that the time spent is equally divided by the inflexion.

The reason for human arm movements to have these characteristics is that the arm movement tends to be smooth and carries the hand from one equilibrium position to another. If objects are held in the hand when moving arms, the bell shape is not symmetric anymore, and there is less time spent before the velocity than that after the peak.

The following characteristics are further found in velocity profiles of falls and other daily activities. All velocities are computed by using equation (1).

$$v = \sqrt{(v_x)^2 + (v_y)^2 + (v_z)^2} - \int G dt \quad (1)$$

wherein $v_x = \int a_x dt$, $v_y = \int a_y dt$, $v_z = \int a_z dt$, and G is the acceleration of gravity.

The velocity computed is only the vertical velocity, instead of the velocities in three axes, because the velocities in the other two axes do not have a unique feature in falls.

Furthermore, the displacement is computed by using equation (2).

$$D = \sqrt{(d_x)^2 + (d_y)^2 + (d_z)^2} - \iint G dt^2$$

$$d_x = \iint a_x dt^2, \, d_y = \iint a_y dt^2, \, d_z = \iint a_z dt^2 \quad (2)$$

The acceleration amplitude is computed by using equation (3).

$$A = \sqrt{(a_x)^2 + (a_y)^2 + (a_z)^2} \quad (3)$$

Figure 3:
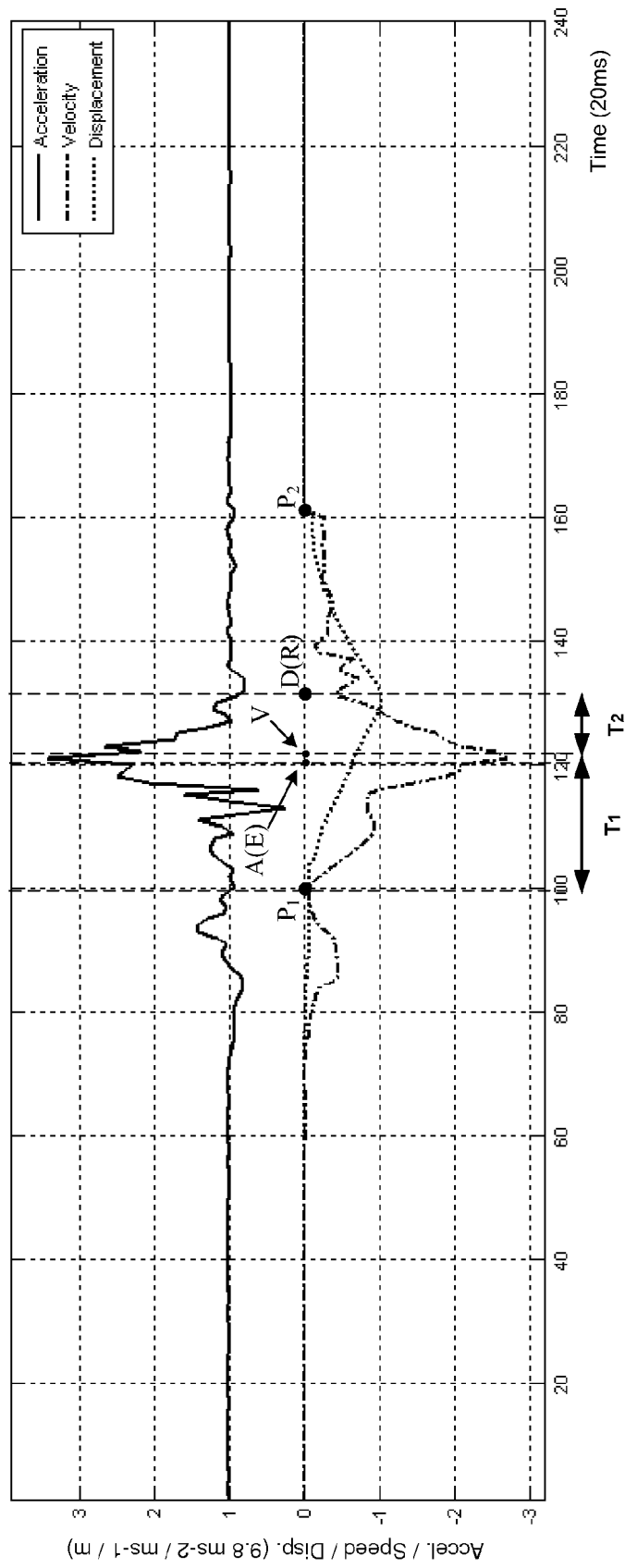
FIG. 3 shows a velocity, acceleration amplitude and displacement profile of a forward fall.

FIG. 3 shows a velocity, acceleration amplitude and displacement profile of a forward fall. As can be seen from this Figure, the lead time $T_1$ is longer than the return time $T_2$.

Here, the lead time $T_1$ is defined as a time interval from an original point $P_1$ of the movement to an extreme point E of the movement, which is the earlier point of: a time point V corresponding to the peak value of the plurality of velocities in the direction of gravity and a time point A corresponding to a peak value of the acceleration amplitudes. These two points are very near to each other. The original point $P_1$ of the movement is a time point preceding and being closest to the extreme point E of the movement where the velocity equals zero.

It is to be noted that the peak value of the plurality of velocities is the minimum velocity if the positive velocity is in the anti-gravity direction and the peak value of the acceleration amplitudes is the maximum acceleration magnitude, not the acceleration in a single axis.

The return time $T_2$ is defined as a time interval from the extreme point E of the movement to a final point R of the movement, which is the earlier point of: a time point $P_2$ succeeding and being closest to the extreme point E of the movement, where the velocity equals zero, and a time point D corresponding to a peak value of the displacements in the direction of gravity. These two points are also very near to each other. The three dot-and-dash lines in FIG. 3 indicate both the lead time $T_1$ and the return time $T_2$.

The reason that $T_1$ is longer than $T_2$ in a fall is that, before the impact (when the velocity reaches the valley), the wrist is moved downward along with the body. $T_1$ is proportional to the falling time of the body. After the impact, the wrist movement is stopped quickly. Even when the wrist bounces on the ground, the time $T_2$ to return to rest is shorter.

Figure 4:
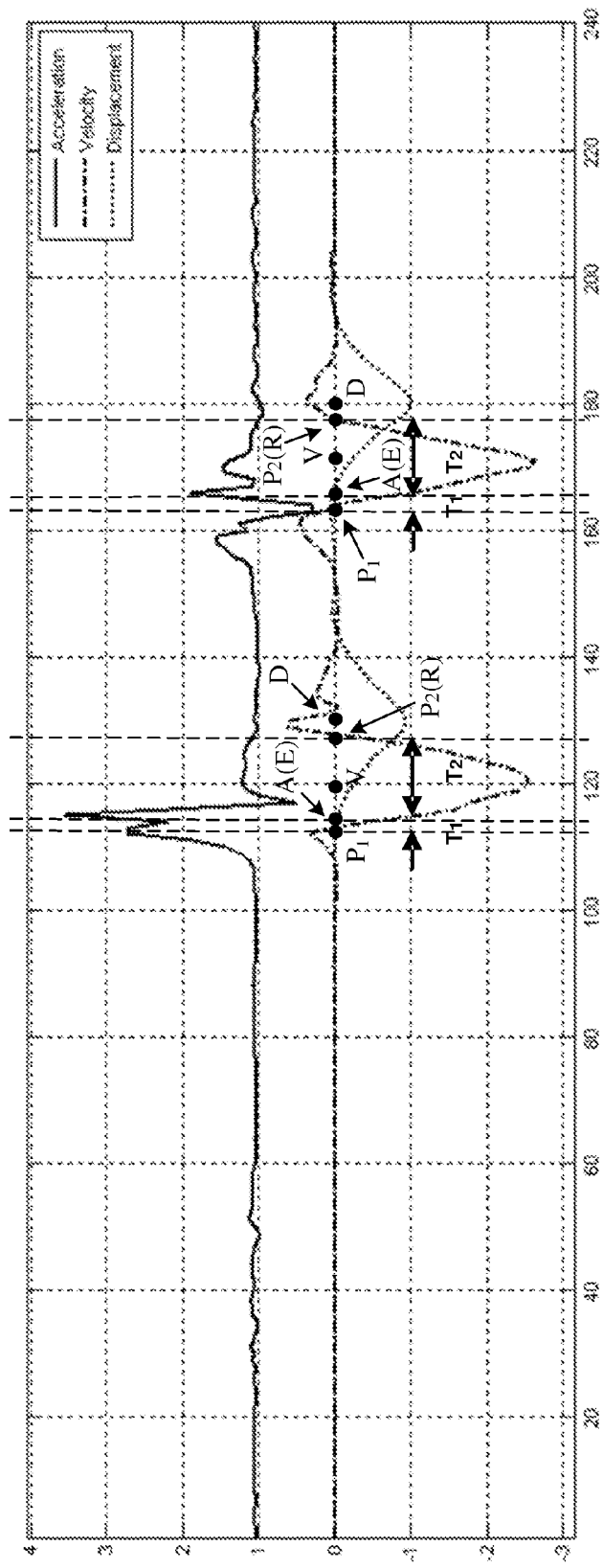
FIG. 4 shows the velocity, acceleration amplitude and displacement profile of wrist torsion.

FIG. 4 shows the velocity, acceleration amplitude and displacement profile of wrist torsion. It can be found that the maximum velocity in the direction of gravity is about 2.5 $ms^{-1}$ (which is larger than 1.3 $ms^{-1}$ threshold used for fall detection in the prior art). However, the lead time $T_1$ is less than the return time $T_2$.

A comparison of the velocity profile of falls and daily activities shows that the lead time is longer than the return time in falls, whereas it is reversed in daily activities.

The invention is based on the above recognition. That is to say, fall detection will be more reliable if a fall is determined when the maximum velocity in the direction of gravity exceeds a threshold and the lead time is longer than the return time.

Figure 5:
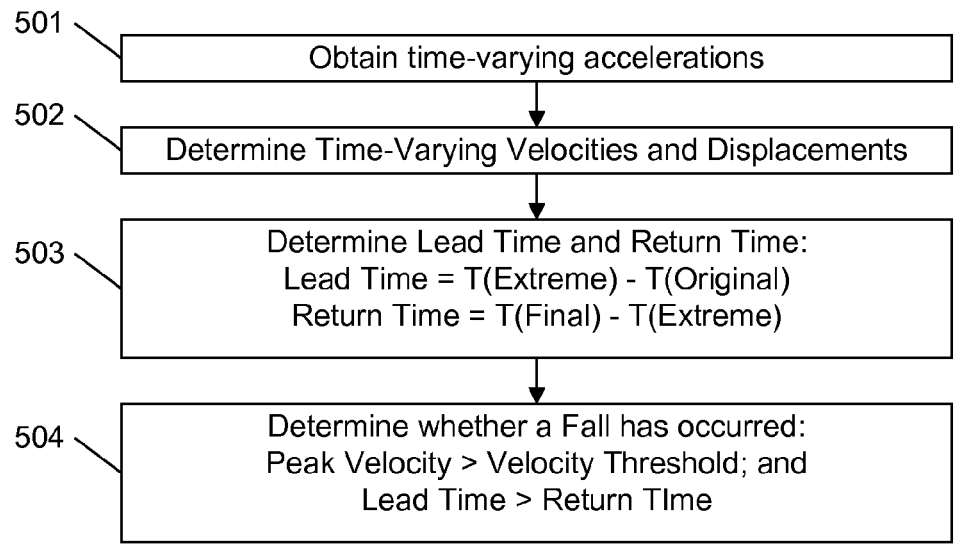
FIG. 5 is a flow chart of the method for detecting the fall of an object in accordance with one embodiment of the present invention.

FIG. 5 is a flow chart of the method for detecting the fall of an object in accordance with one embodiment of the present invention.

As shown in FIG. 5, the method for detecting the fall of an object according to the present invention comprises a step 501 of acquiring a plurality of time-varying accelerations associated with a movement of said object. The plurality of time-varying accelerations may be detected by the accelerometer incorporated in the apparatus for fall detection.

The method further comprises a step 502 of computing a plurality of respective velocities and displacements in the direction of gravity, based on the plurality of time-varying accelerations.

In an embodiment of the invention, the computing step 502 adopts the above equations (1) and (2).

The method further comprises a step 503 of determining lead time and return time of the movement based on the plurality of accelerations, velocities and displacements, wherein the lead time equals a time interval from an original point of the movement to an extreme point of the movement, and the return time equals a time interval from the extreme point of the movement to a final point of the movement.

In an embodiment of the invention, the original point of the movement is a time point preceding and being closest to the extreme point of the movement where velocity equals zero.

The method further comprises a step 504 of determining whether the fall of said object occurs, based on whether a peak value of the velocities is larger than a predetermined threshold value and whether the lead time is longer than the return time.

In an embodiment of the invention, the predetermined threshold value is 1.3 ms$^{-1}$ and it is determined that the fall occurs when the velocities have a peak value which is larger than 1.3 ms$^{-1}$ and the lead time is longer than the return time.

Since determination of a fall does not only include a criterion that the maximum velocity in the direction of gravity must exceed a threshold but also includes a criterion that the lead time must be longer than the return time, wherein the lead time and the return time representing the difference between the fall and other daily activities can be used as a feature to distinguish falls from other activities, the rate of false alarms is reduced, resulting in an improved reliability of fall detection.

Furthermore, a comparison of the velocity profile of falls and daily activities in FIGS. 3 and 4 shows that the velocity profile in daily activities is smoother (similar to a bell shape) than the one in falls. In mathematics, the smoothness of a function can be measured by its 2nd-order derivative. Equations (4) and (5) show how to compute the 1st-order derivative D and the 2nd-order derivative J.

$$D_n = \frac{v_n - v_{n-1}}{t_n - t_{n-1}} \quad (4)$$

$$J_n = \frac{D_n - D_{n-1}}{t_n - t_{n-1}} \quad (5)$$

wherein $t_{n-1}$ and $t_n$ are the times of neighboring samples.

It is advantageous to use equations (2) and (4) to compute the 1st-order derivative of the velocity instead of using the acceleration data directly, because equation (2) works as a filter smoothing the acceleration data.

If the function is smooth, its 1st-order derivative does not change much within a very short period of time. Therefore, its 2nd-order derivative should not be too large, which means that the J value should be less than a threshold when the sampling interval is small enough. Since daily activities have a smoother velocity profile than falls, the 2nd-order derivative of the velocity for falls should be larger than a threshold, such as 2 ms$^{-3}$ when the sampling rate is 50 Hz.

Figure 6:
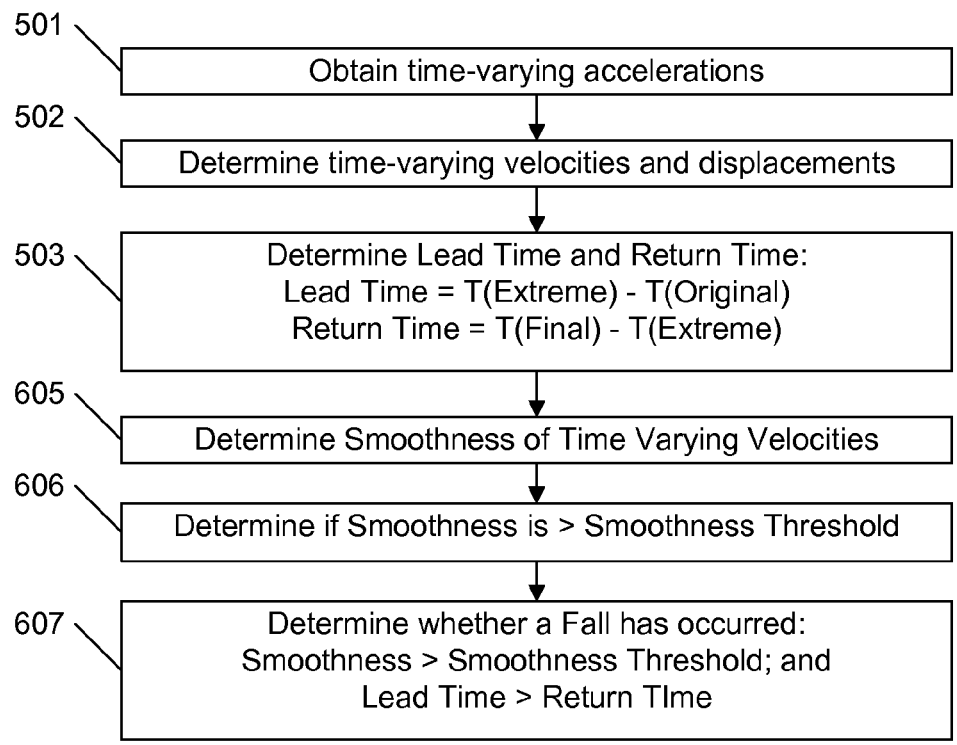
FIG. 6 is a flow chart of the method for detecting the fall of an object in accordance with another embodiment of the present invention.

FIG. 6 is a flow chart of the method for detecting the fall of an object in accordance with another embodiment of the present invention.

The method comprises steps 501 to 503 that are similar to the steps elucidated in the embodiment described above. The method further comprises a step 605 of computing smoothness of time-varying velocities based on the plurality of velocities.

In an embodiment, the method further comprises a step 606 of determining whether the smoothness is larger than a predefined smoothness threshold.

In an embodiment, the method further comprises a step 607 of determining that the fall of said object occurs when the smoothness is larger than the predefined smoothness threshold and the lead time is longer than the return time.

Since, in addition to the lead time and the return time representing the difference between the fall and other daily activities, the smoothness of the velocity profile can also be used as a feature to distinguish falls from other activities, the reliability of fall detection is further improved.

The procedure for calculating the lead time $T_1$ and the return time $T_2$ will hereinafter be described in detail with reference to FIG. 7.

Figure 7:
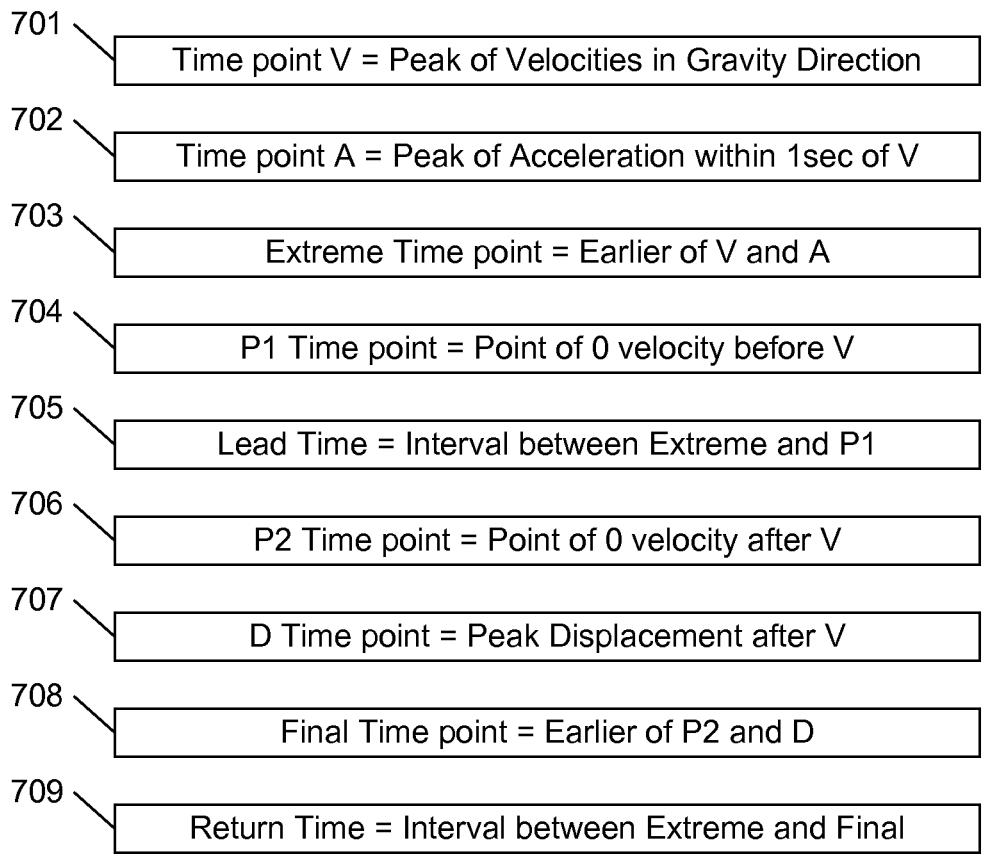
FIG. 7 shows the procedure for calculating the lead time $T_1$ and the return time $T_2$.

FIG. 7 shows the procedure for calculating the lead time $T_1$ and the return time $T_2$. As shown, the procedure is carried out on the basis of the plurality of accelerations, velocities and displacements in accordance with an embodiment of the present invention. The procedure will be easily understood in combination with FIGS. 3 and 4.

First, in step 701, a time point V corresponding to the peak value of the plurality of velocities in the direction of gravity is determined.

Then, in step 702, it searches the time point A corresponding to a peak value of the acceleration amplitude within 1 second to the V point.

In step 703, use is made of the earlier point of V and A as the extreme point E.

In step 704, it searches back from the V point until the time point of zero velocity, $P_1$.

In step 705, the time interval between points $P_1$ and E is calculated as the lead time $T_1$.

In step 706, it searches forward from the V point until the next time point of zero velocity $P_2$.

In step 707, it searches forward from the V point until the time point D corresponding to a peak value of the displacements in the direction of gravity.

In step 708, use is made of the earlier point of $P_2$ and D as the final point R.

Finally, in step 709, the time interval between points E and R is calculated as the return time $T_2$.

Figure 8:
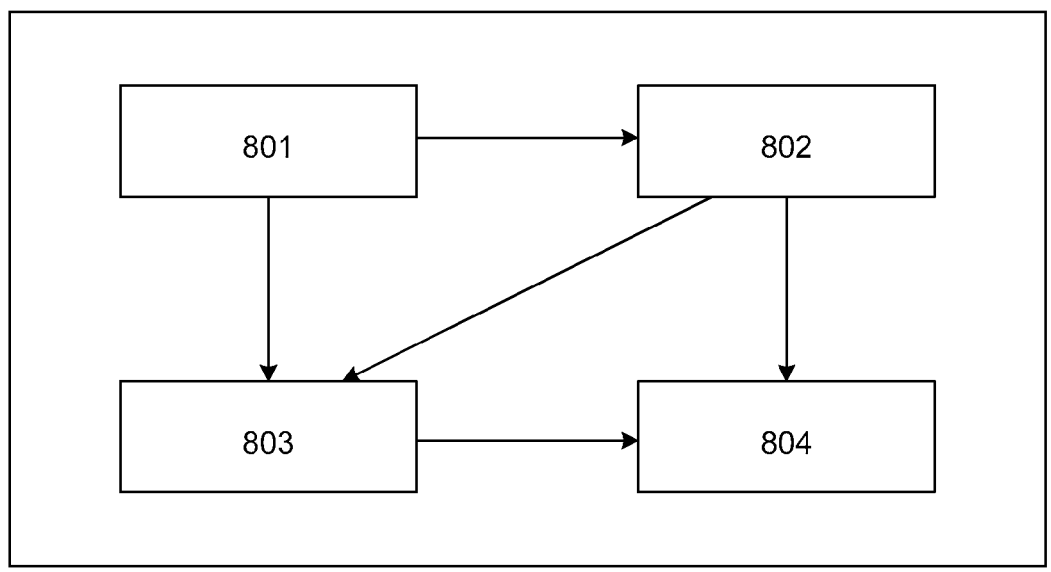
FIG. 8 is a schematic block diagram of the apparatus for detecting the fall of an object in accordance with one embodiment of the present invention.

FIG. 8 is a schematic block diagram of the apparatus for detecting the fall of an object in accordance with one embodiment of the present invention. The apparatus comprises an acquiring unit 801 configured to acquire a plurality of time-varying accelerations associated with a movement of said object. The first unit 801 may execute step 501 described hereinbefore.

The apparatus further comprises a first computing unit 802 configured to compute a plurality of respective velocities and displacements in the direction of gravity, based on the plurality of time-varying accelerations. The first computing unit 802 may execute step 502 described hereinbefore.

The apparatus further comprises a first determining unit 803 configured to determine lead time and return time of the movement, based on the plurality of accelerations and the plurality of velocities and displacements. The first determining unit 803 may execute step 503 described hereinbefore.

The apparatus further comprises a second determining unit 804 configured to determine whether a fall of said object occurs, based on whether a peak value of the velocities is larger than a predefined threshold value and whether the lead time is longer than the return time. The second determining unit 804 may execute step 504 described hereinbefore.

Figure 9:
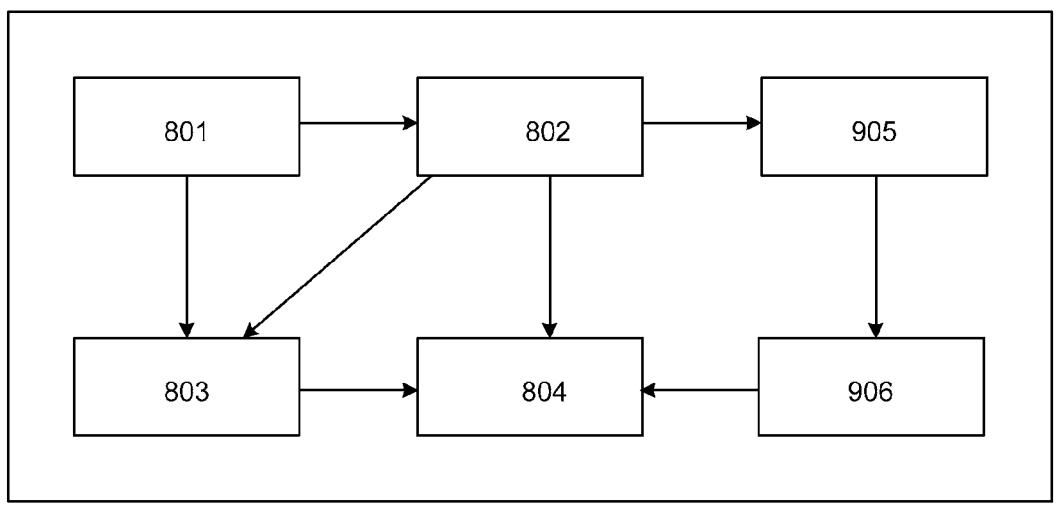
FIG. 9 is a schematic block diagram of the apparatus for detecting the fall of an object in accordance with another embodiment of the present invention.

FIG. 9 is a schematic block diagram of the apparatus for detecting the fall of an object in accordance with another embodiment of the present invention. The apparatus comprises units 801-804 that are similar to the units of the embodiment described above. The apparatus further comprises a second computing unit 905 configured to compute smoothness of time-varying velocities based on the plurality of velocities. The second computing unit 905 may execute step 605 described hereinbefore.

The apparatus further comprises a third determining unit 906 configured to determine whether the smoothness is larger than a predefined smoothness threshold. The third determining unit 906 may execute step 606 described hereinbefore and the second determining unit 804 may execute step 607 described hereinbefore.

The invention can be implemented by means of hardware comprising several distinct elements, and by means of a suitable computer program. In the device claim enumerating several means, several of these means can be embodied by one and the same item of hardware. The mere fact that certain measures are recited in mutually different dependent claims does not indicate that a combination of these measures cannot be used to advantage.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim or in the description. The article "a" or "an" preceding an element does not exclude the presence of a plurality of such elements. In the apparatus claims enumerating several units, several of these units can be embodied by one and the same item of software and/or hardware. Use of the words first, second and third, etc. does not indicate any ordering. These words are to be interpreted as names.

The invention claimed is:

1. A method for detecting the fall of an object, comprising:
    storing a plurality of time-varying accelerations associated with a movement of the object in a memory element;
    computing, by a processor coupled to the memory element, a plurality of respective velocities and displacements in the direction of gravity, based on the plurality of time-varying accelerations;
    determining, by the processor, a lead time and a return time of the movement, based on the plurality of accelerations, velocities and displacements, wherein the lead time equals a time interval from an original point ($P_1$) of the movement to an extreme point (E) of the movement, and the return time equals a time interval from the extreme point (E) of the movement to a final point (R) of the movement; and
    determining, by the processor, whether the fall of the object occurs, based on whether a peak value of the velocities is larger than a predefined threshold value and whether the lead time is longer than the return time.

2. A method as claimed in claim 1, wherein the extreme point (E) of the movement is an earlier of: a time point (V) corresponding to the peak value of the plurality of velocities in the direction of gravity and a time point (A) corresponding to a peak value of the acceleration amplitudes.

3. A method as claimed in claim 2, wherein the original point ($P_1$) of the movement is a time point preceding and being closest to the extreme point (E) of the movement where velocity equals zero.

4. A method as claimed in claim 3, wherein the final point (R) of the movement is an earlier of: a time point ($P_2$) succeeding and being closest to the extreme point (E) of the movement where velocity equals zero and a time point (D) corresponding to a peak value of the displacements in the direction of gravity.

5. A method as claimed in claim 1, including:
    computing smoothness of time-varying velocities based on the plurality of velocities;
    determining whether the smoothness is larger than a predefined smoothness threshold; and
    determining that the fall of the object occurs when the smoothness is larger than the predefined smoothness threshold.

6. A method as claimed in claim 5, wherein the smoothness is given by the 2nd-order derivative of the plurality of velocities and is computed as:

$$D_n = \frac{v_n - v_{n-1}}{t_n - t_{n-1}} \text{ and}$$

$$J_n = \frac{D_n - D_{n-1}}{t_n - t_{n-1}}$$

wherein $t_{n-1}$ and $t_n$ are neighboring sampling time points, $v_{n-1}$ and $v_n$ are neighboring sampling velocities, and $D_n$ and $J_n$ are the 1st-order derivative and the 2nd-order derivative, respectively, for the plurality of velocities.

7. A method as claimed in claim 6, wherein the accelerations include accelerations $a_x$, $a_y$, $a_z$ in x, y, z directions, respectively, and the velocities are given by $$v = \sqrt[t]{(v_x)^2 + (v_y)^2 + (v_z)^2} - \int G dt$$

wherein $v_x = \int a_x dt$, $v_y = \int a_y dt$, $v_z = \int a_z dt$, and G is the acceleration of gravity.

8. An apparatus for detecting the fall of an object, comprising:
    an acquiring unit configured to acquire a plurality of time-varying accelerations associated with a movement of the object;
    a first computing unit configured to compute a plurality of respective velocities and displacements in the direction of gravity, based on the plurality of time-varying accelerations;
    a first determining unit configured to determine lead time and return time of the movement, based on the plurality of accelerations, velocities and displacements, wherein the lead time equals a time interval from an original point ($P_1$) of the movement to an extreme point (E) of the movement, and the return time equals a time interval from the extreme point (E) of the movement to a final point (R) of the movement; and
    a second determining unit configured to determine whether a fall of the object occurs, based on whether a peak value of the velocities is larger than a predefined threshold value and whether the lead time is longer than the return time.

9. An apparatus as claimed in claim 8, wherein the extreme point (E) of the movement is an earlier of: a time point (V) corresponding to the peak value of the plurality of velocities in the direction of gravity and a time point (A) corresponding to a peak value of the acceleration amplitudes.

10. An apparatus as claimed in claim 9, wherein the original point ($P_1$) of the movement is a time point preceding and being closest to the extreme point (E) of the movement where velocity equals zero, and the final point (R) of the movement is an earlier of: a time point ($P_2$) succeeding and being closest to the extreme point (E) of the movement, where velocity equals zero, and a time point (D) corresponding to a peak value of the displacements in the direction of gravity.

11. An apparatus as claimed in claim 8, further comprising:
    a second computing unit configured to compute smoothness of time-varying velocities based on the plurality of velocities;
    a third determining unit configured to determine whether the smoothness is larger than a predefined smoothness threshold; and
    wherein the second determining unit is further configured to determine that the fall of the object occurs when the smoothness is larger than the predefined smoothness threshold.

12. An apparatus as claimed in claim 8, wherein the acquiring unit is a 3D accelerometer.

13. An apparatus as claimed in claim 8, further comprising a preprocessor for preprocessing the plurality of accelerations, velocities and displacements.

14. A non-transitory computer readable medium that includes a program for detecting the fall of an object that, when executed by a processor, causes the processor to:
   acquire a plurality of time-varying accelerations associated with a movement of the object;
   compute a plurality of respective velocities and displacements in the direction of gravity, based on the plurality of time-varying accelerations;
   determine a lead time and a return time of the movement, based on the plurality of accelerations, velocities and displacements, wherein the lead time equals a time interval from an original point ($P_1$) of the movement to an extreme point (E) of the movement, and the return time equals a time interval from the extreme point (E) of the movement to a final point (R) of the movement; and
   determine whether the fall of the object occurs, based on whether a peak value of the velocities is larger than a predefined threshold value and whether the lead time is longer than the return time.

15. The medium of claim 14, wherein the extreme point (E) of the movement is an earlier point between a time point (V) corresponding to the peak value of the plurality of velocities in the direction of gravity and a time point (A) corresponding to a peak value of the acceleration amplitudes.

16. The medium of claim 14, wherein the final point (R) of the movement is an earlier of: a time point ($P_2$) succeeding and being closest to the extreme point (E) of the movement where velocity equals zero and a time point (D) corresponding to a peak value of the displacements in the direction of gravity.

17. The medium of claim 14, wherein the program that causes the processor to:
   compute smoothness of time-varying velocities based on the plurality of velocities;
   determine whether the smoothness is larger than a predefined smoothness threshold; and
   determine that the fall of the object occurs when the smoothness is larger than the predefined smoothness threshold.

18. The medium of claim 17, wherein the smoothness is given by the 2nd-order derivative of the plurality of velocities and is computed as:

$$D_n = \frac{v_n - v_{n-1}}{t_n - t_{n-1}} \text{ and}$$

$$J_n = \frac{D_n - D_{n-1}}{t_n - t_{n-1}}$$

wherein $t_{n-1}$ and $t_n$ are neighboring sampling time points, $v_{n-1}$ and $v_n$ are neighboring sampling velocities, and $D_n$ and $J_n$ are the 1st-order derivative and the 2nd-order derivative, respectively, for the plurality of velocities.

19. The medium of claim 14, wherein the original point ($P_1$) of the movement is a time point preceding and being closest to the extreme point (E) of the movement where velocity equals zero.

20. An apparatus as claimed in claim 8, wherein the smoothness is given by the 2nd-order derivative of the plurality of velocities and is computed as:

$$D_n = \frac{v_n - v_{n-1}}{t_n - t_{n-1}} \text{ and}$$

$$J_n = \frac{D_n - D_{n-1}}{t_n - t_{n-1}}$$

wherein $t_{n-1}$ and $t_n$ are neighboring sampling time points, $v_{n-1}$ and $v_n$ are neighboring sampling velocities, and $D_n$ and $J_n$ are the 1st-order derivative and the 2nd-order derivative, respectively, for the plurality of velocities.

* * * * *